(12) United States Patent
Zhao et al.

(10) Patent No.: US 9,930,445 B2
(45) Date of Patent: Mar. 27, 2018

(54) INTERFERENCE CANCELLATION FOR THROAT MICROPHONE

(71) Applicant: INVENSENSE, INC., San Jose, CA (US)

(72) Inventors: Jia Zhao, ShangHai (CN); Yang Pan, ShangHai (CN); Yuanjin Li, ShangHai (CN); Dan Li, ShangHai (CN); Hao Ding, ShangHai (CN)

(73) Assignee: INVENSENSE, INC., San Jose, CA (US)

( * ) Notice: Subject to any disclaimer, the term of this patent is extended or adjusted under 35 U.S.C. 154(b) by 271 days.

(21) Appl. No.: 14/737,946

(22) Filed: Jun. 12, 2015

(65) Prior Publication Data

US 2016/0366513 A1    Dec. 15, 2016

(51) Int. Cl.
| H04R 25/00 | (2006.01) |
| H04R 1/46 | (2006.01) |
| H04M 1/05 | (2006.01) |
| H04R 1/10 | (2006.01) |
| A61B 5/00 | (2006.01) |
| G10L 21/0216 | (2013.01) |
| H04R 1/14 | (2006.01) |

(52) U.S. Cl.
CPC ............ *H04R 1/46* (2013.01); *A61B 5/6822* (2013.01); *G10L 21/0216* (2013.01); *H04M 1/05* (2013.01); *H04R 1/105* (2013.01); *H04R 1/1091* (2013.01); *H04R 25/554* (2013.01); *H04R 1/14* (2013.01); *H04R 2499/11* (2013.01)

(58) Field of Classification Search
CPC ........ H04R 1/105; H04R 1/1091; H04R 1/14; H04R 1/16; H04R 1/46; H04R 25/554; H04M 1/05; A61B 5/4803; A61B 5/4836; A61B 5/6822
USPC ............. 381/309, 326, 151, 380, 71.1, 71.2; 600/301, 586; 181/130, 131
See application file for complete search history.

(56) References Cited

U.S. PATENT DOCUMENTS

| 2012/0172676 A1* | 7/2012 | Penders ................. A61B 7/003 600/301 |
| 2015/0305920 A1* | 10/2015 | Patel ........................ A61F 5/58 381/151 |

* cited by examiner

*Primary Examiner* — Huyen D Le
(74) *Attorney, Agent, or Firm* — Amin, Turocy & Watson, LLP

(57) ABSTRACT

A throat microphone may include one or more transducers that are in contact with the skin in the region of the larynx of person, and may provide a vibration signal to a processing unit. The vibration signal may also include energy and information relating to secondary physiological phenomena such as breathing and heartbeat, in addition to the desired sonic signal. The processing unit may utilize information relating to the secondary physiological phenomena to control a filter that outputs the desired sonic signal.

9 Claims, 7 Drawing Sheets

INTERFERENCE CANCELLATION FOR THROAT MICROPHONE

TECHNICAL FIELD

The subject disclosure relates to throat microphones, and more particularly, to processing of vibration signals from throat microphones.

BACKGROUND

By way of background, microphones may be used to receive and transmit acoustic signals, and in particular, audible signals. However, in many noisy environments it may be difficult to discern an audible signal of interest such as human speech from audible noise signals such as background noise, wind, traffic, construction, music, crowd noise, etc. As wireless communication technology such as cell phones, smart phones, smart watches, and other similar devices have become more ubiquitous, users are able to have conversations untethered to fixed locations and may more frequently encounter such audible noise signals that make it difficult discern speech.

Throat microphones may be in contact with a user's throat and may sense vibrations of the skin of the throat. Those vibrations may include, inter alia, vibrations that are associated with a sonic signal (e.g., speech) of the user. Because the throat microphone is not in contact with typical sources of audible noise signals, it may not sense vibrations from those sources. To the extent that these audible noise signals are not included in the vibration signal of the throat microphone, it may be easier to discern the audible signal of interest such as human speech. However, speech is not the only source of vibration that may be received by a throat microphone, and other sources of vibration may make it difficult to discern the sonic signal from other aspects of the vibration signal.

SUMMARY

The following presents a simplified summary of the specification to provide a basic understanding of some aspects of the specification. This summary is not an extensive overview of the specification. It is intended to neither identify key or critical elements of the specification nor delineate any scope particular to any embodiments of the specification, or any scope of the claims. Its sole purpose is to present some concepts of the specification in a simplified form as a prelude to the more detailed description that is presented later.

In a non-limiting example, a method for analyzing vibrations of a throat area of a person can comprise receiving a vibration signal and identifying a characteristic of the vibration signal that is associated with a secondary physiological phenomena. The method can also comprise determining a filter control parameter based on the characteristic and modifying a setting of a filter based on the filter control parameter. The method can further comprise filtering the vibration signal with the filter, wherein the filtered vibration signal is representative of a desired physiological signal.

In another non-limiting example, a system for providing a desired physiological signal based on vibrations of a throat area of a person can comprise a vibration sensor and a processor. The system can also comprise that the processor is configured to receive a vibration signal from the vibration sensor, identify a characteristic of the vibration signal that is associated with a secondary physiological phenomena, determine a filter control parameter based on the characteristic, and provide the desired physiological signal based on the filter control parameter and the vibration signal. The system can further comprise a communication unit coupled to the processor and in communication with a device, wherein the communication unit transmits the sonic signal to the device.

In another non-limiting example, an apparatus for analyzing vibrations of a throat area of a person can comprise a control signal source configured to receive a vibration signal from a vibration sensor, identify a characteristic of the vibration signal that is associated with a secondary physiological phenomena, and determine a filter control parameter based on the characteristic. The apparatus can also comprise a filter configured to receive the vibration signal and provide a filtered vibration signal representative of a desired physiological signal, wherein a setting of the filter is modified based on the filter control parameter.

The following description and the drawings contain certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

BRIEF DESCRIPTION OF THE DRAWINGS

Numerous aspects, embodiments, objects and advantages of the present invention will be apparent upon consideration of the following detailed description, taken in conjunction with the accompanying drawings, in which like reference characters refer to like parts throughout, and in which.

DETAILED DESCRIPTION

Overview

Figure 1:
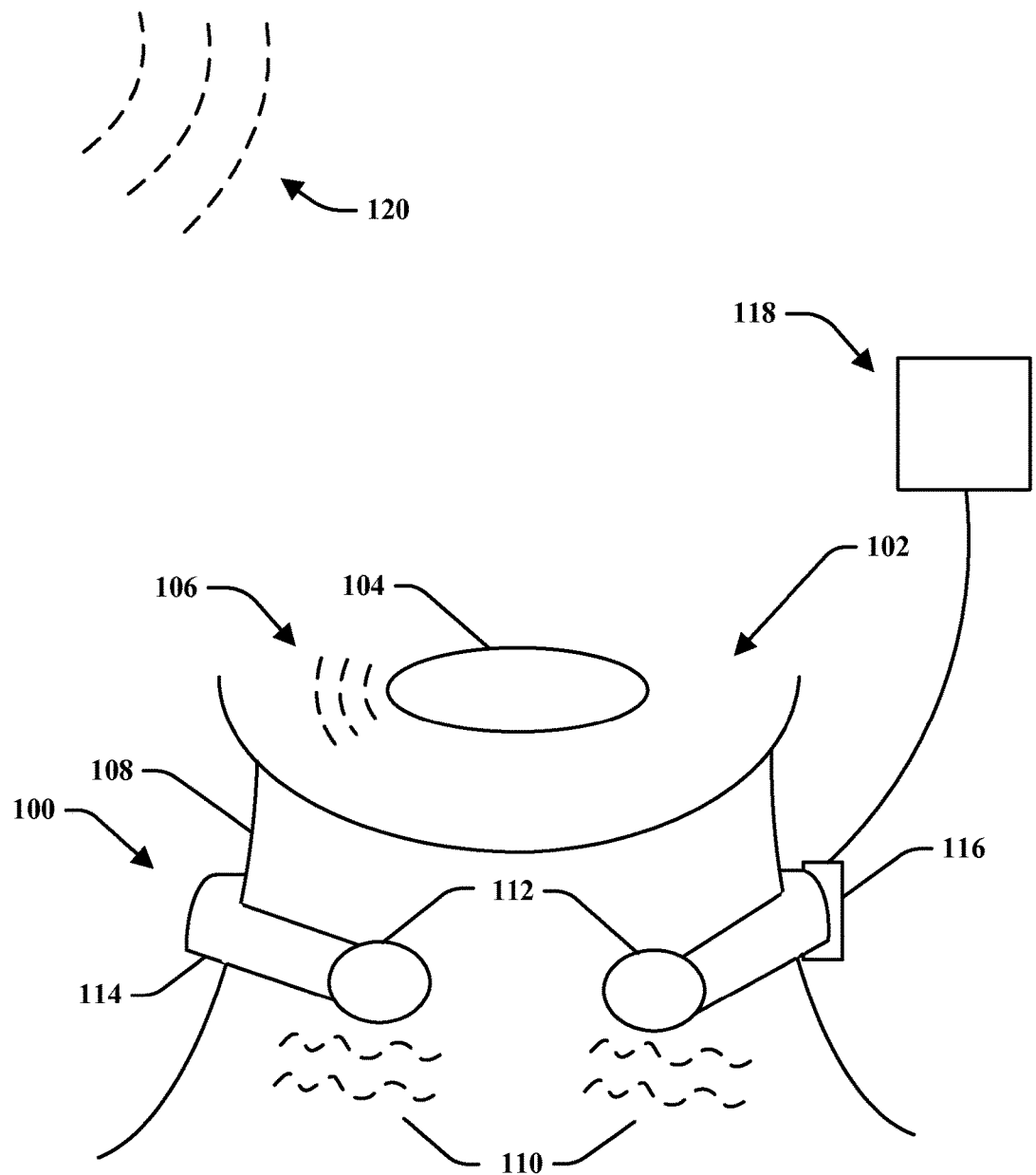
FIG. 1 depicts a non-limiting depiction of an exemplary throat microphone according to various non-limiting aspects of the subject disclosure.

While a brief overview is provided, certain aspects of the subject disclosure are described or depicted herein for the purposes of illustration and not limitation. Thus, variations of the disclosed embodiments as suggested by the disclosed apparatuses, systems and methodologies are intended to be encompassed within the scope of the subject matter disclosed herein.

Aspects of systems, apparatuses or processes explained in this disclosure can constitute machine-executable components embodied within machine(s), hardware components, or hardware components in combination with machine executable components, e.g., embodied in one or more computer readable mediums (or media) associated with one or more machines. Such components, when executed by the one or more machines, e.g., computer(s), computing device(s), virtual machine(s), etc., can cause the machine(s) to perform the operations described. While the various components are illustrated as separate components, it is noted that the various components can be comprised of one or more other components. Further, it is noted that the embodiments can comprise additional components not shown for sake of brevity. Additionally, various aspects described herein may be performed by one device or two or more devices in communication with each other.

To that end, one or more processors can execute code instructions stored in memory, for example, volatile memory and/or nonvolatile memory. By way of illustration, and not limitation, nonvolatile memory can include read only memory (ROM), programmable ROM (PROM), electrically programmable ROM (EPROM), electrically erasable PROM (EEPROM), or flash memory. Volatile memory can include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory (e.g., data stores, databases) of the subject systems and methods is intended to comprise, without being limited to, these and any other suitable types of memory.

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units.

Various embodiments described herein provide for processing of a vibration signal from a throat microphone in order to provide a sonic signal that may include speech information. The throat microphone can include a transducer that is in contact with the skin in the region of the larynx. The transducer vibrates in response to the motion of the larynx due to speech as well as other physiological phenomena, and that vibration is converted into a vibration signal. The vibration signal may be provided to a filter, the filter having control parameters that allow the filter to remove aspects of the vibration signal that do not correspond to the sonic signal.

In an embodiment, the filter control parameter may be based on a characteristic of a secondary physiological phenomena that may also cause vibration of the transducer of the throat microphone. Examples of secondary physiological phenomena may include breathing and heartbeat. These secondary physiological phenomena may have frequencies that differ from the frequency of a sonic signal, and a frequency associated with one or more secondary physiological signals may be used to determine a characteristic such as a cutoff frequency for a high-pass filter, which may be used to set a filter control parameter.

The systems and methods of the present invention can provide for a filter bank to identify the characteristic of the secondary physiological signal, which may include plurality of band-pass filters having a set of frequency ranges associated with typical secondary physiological phenomena, but not including frequencies associates with a sonic signal. Based on the output energy of the band-pass filters the frequencies of one or more secondary physiological signals may be determined. This may be used to identify a cutoff frequency for a filter, which may be used to set the filter control parameter of the filter (e.g., a shift value corresponding to the cutoff frequency of the high-pass filter). In some embodiments, values for the secondary physiological signals, such as respiration rate or heart rate, may be determined based on the energies output from the filter bank.

Various other configurations or arrangements are described herein. It is noted that the various embodiments can include other components and/or functionality. It is further noted that the various embodiments can be included in larger systems, including, tactical communication systems, smart phones or other cellular phones, wearables (e.g., watches, headphones, etc.), tablet computers, electronic reader devices (i.e., e-readers), laptop computers, desktop computers, monitors, digital recording devices, appliances, home electronics, handheld gaming devices, remote controllers (e.g., video game controllers, television controllers, etc.), automotive devices, personal electronic equipment, medical devices, industrial systems, cameras, and various other devices or fields.

Exemplary Embodiments

Various aspects or features of the subject disclosure are described with reference to the drawings, wherein like reference numerals are used to refer to like elements throughout. In this specification, numerous specific details are set forth in order to provide a thorough understanding of the subject disclosure. It should be understood, however, that the certain aspects of disclosure may be practiced without these specific details, or with other methods, components, parameters, etc. In other instances, well-known structures and devices are shown in block diagram form to facilitate description and illustration of the various embodiments.

Accordingly, FIG. 1 provides a non-limiting depiction of an exemplary throat microphone 100 according to various non-limiting aspects of the subject disclosure. It is to be appreciated that throat microphone 100 can be used in connection with implementing one or more systems or components shown and described with reference to other figures disclosed herein. Further, it is noted that the embodiments can comprise additional components not shown for sake of brevity. Additionally, various aspects described herein may be performed by one device or two or more devices in communication with each other.

In an embodiment, throat microphone 100 may include one or more transducers 112, a locating structure 114, and a processing unit 116. Although the exemplary throat microphone 100 is described as including two transducers 112, it will be understood that any suitable number of transducers 112 (e.g., one transducers, two or more transducers) may be used in accordance with the exemplary embodiments described herein. Locating structure 114 of throat microphone 100 may attach to or around a neck 108 of a person 102, in a manner that places the transducers 112 in contact with the skin of person 102 in the larynx region of the neck 108. In an embodiment, processing unit 116 may be attached to locating structure 114 of the throat microphone, although it will be understood that processing unit 116 may be located in any suitable manner that results in communicable coupling to the vibration signal output by the one or more transducers 112.

When a person 102 speaks, audible speech 106 may be provided from the mouth 104, which may be audible to a listener, microphone, or other device in physical proximity to the person 102. However, audible noise signals 120 such as background noise, wind, traffic, construction, music, and crowd noise may also be heard by a listener, microphone, or other device that is in physical proximity to the person 102. In these noisy environments it may be difficult to hear, discern, and/or understand the audible speech 106, even if the listener, microphone, or other device is located in very close proximity to the mouth 104 of person 102.

The transducers 112 of throat microphone 100 may provide a vibration signal in response to vibrations 110 of the skin that is contact with transducers 112. The information provided by this vibration signal will not include any noise source that does not cause vibrations 110 of the skin that is in contact with the transducers. Accordingly, the vibration signal provided by transducers 112 typically will not include significant energy and information from audible noise signals 120 such as background noise, wind, traffic, construction, music, or crowd noise. In some embodiments, the vibration signal provided by transducers 112 may primarily include energy and information related to physiological phenomena that cause vibration of the skin that is in contact with transducers 112. When the transducers 112 are located in the region of the larynx this will include vibrations resulting from human speech, which may be used to generate a sonic signal (e.g., by processing unit 116) as described herein.

In some embodiments, other secondary physiological phenomena may also result in vibration of the skin that is in contact with transducers 112. Although it will be understood that vibration related to any suitable secondary physiological phenomena may be picked up by transducers 112, in some embodiments such secondary physiological phenomena may include the breathing or heartbeat of person 102. The vibrations caused by these secondary physiological phenomena may result in noise that may interfere with the desired sonic signal caused by vibrations of the larynx. As described herein, a processor of processing unit 116 may include a control signal source that determines one or more filter control parameters based on a characteristic of the vibration signal that is associated with one or more secondary physiological phenomena. The filter control parameter may be provided to a filter that filters the vibration signal in a manner that reduces the energy and information associated with the secondary physiological phenomena, resulting in an output signal that is representative of the desired sonic signal.

In an embodiment, processing unit 116 may be in communication with a device 118 to provide information including the desired sonic signal. Although a single device is depicted in FIG. 1, it will be understood that a processing unit 116 of throat microphone 100 may be in communication with any suitable number and types of devices 118. Although it will be understood that any suitable device 118 may be in communication with processing unit 116 of throat microphone 100 to receive the desired sonic signal, exemplary devices include earpieces, headsets, short range radio devices, tactical communication systems, smart phones or other cellular phones, wearable devices (e.g., watches, headphones, etc.), tablet computers, electronic reader devices (i.e., e-readers), laptop computers, desktop computers, monitors, digital recording devices, appliances, home electronics, handheld gaming devices, remote controllers (e.g., video game controllers, television controllers, etc.), automotive devices, personal electronic equipment, medical devices, industrial systems, and cameras. Processing unit 116 of throat microphone 100 may communicate with one or more devices 118 in any suitable manner, including wired (e.g., hard wired, direct acoustic wiring, Ethernet, USB, FireWire, I2C, UART, Thunderbolt, etc.) or wireless (e.g., short range radio, satellite, WiFi, Bluetooth, cellular networks, etc.) connections.

Figure 2:
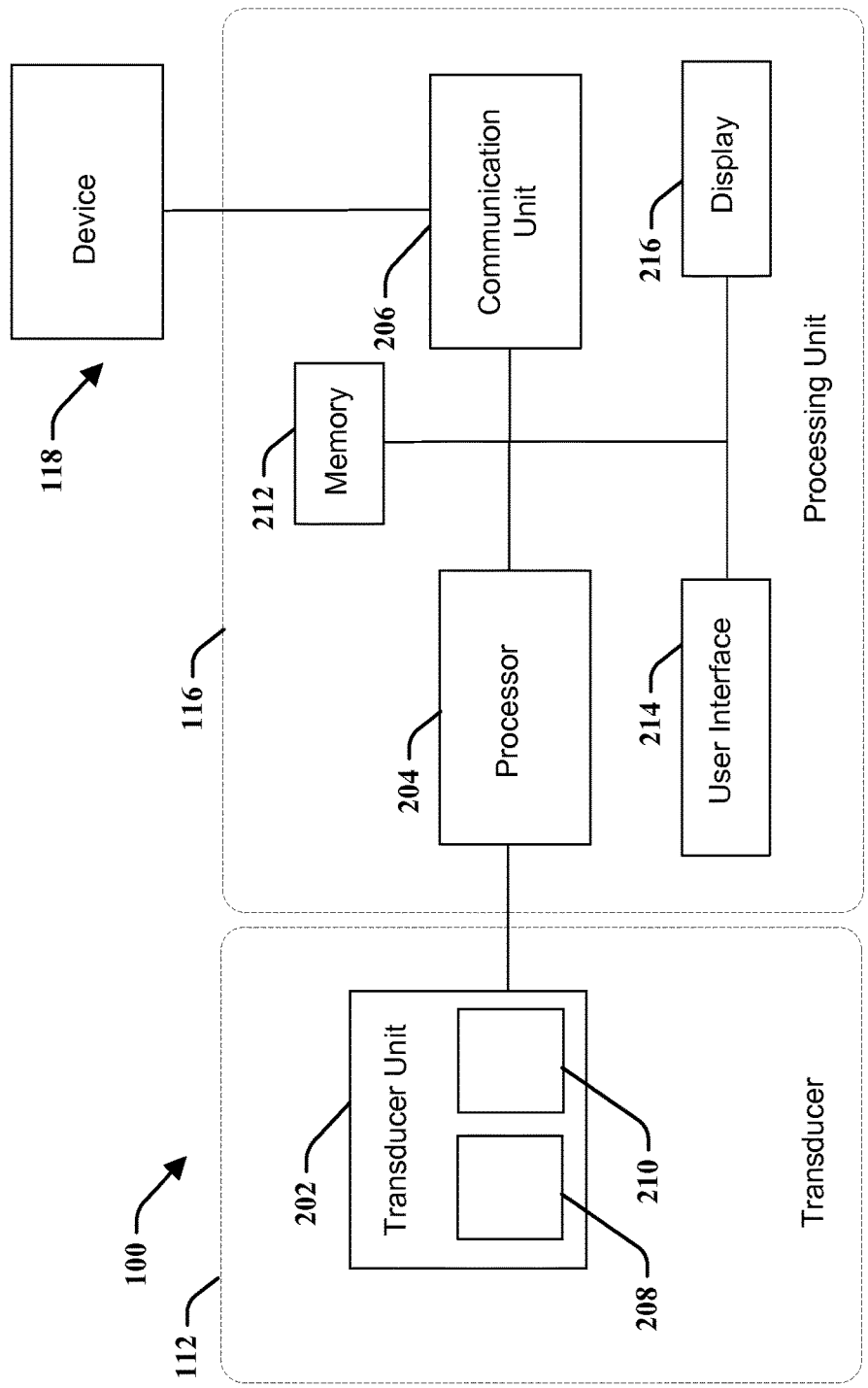
FIG. 2 depicts a non-limiting schematic diagram of components of an exemplary throat microphone according to various non-limiting aspects of the subject disclosure.

Turning now to FIG. 2, illustrated is a non-limiting schematic diagram of components of an exemplary throat microphone 100 according to various non-limiting aspects of the subject disclosure. It is to be appreciated that the components of throat microphone 100 can be used in connection with implementing one or more systems or components shown and described with reference to other figures disclosed herein. Further, it is noted that the embodiments can comprise additional components not shown for sake of brevity. Additionally, various aspects described herein may be performed by one device or two or more devices in communication with each other. For example, one or more components of processing unit 116 may be performed by processing circuitry of transducer 112, or remotely by a device 118.

In an embodiment, each transducer 112 may include a transducer unit 202 that includes a vibration sensor 208 and an energy converter 210. Although it will be understood that any suitable vibration sensor 208 and energy converter 210 may be used in accordance with the present disclosure, exemplary embodiments may include piezoelectric, optical, or microelectromechanical system (MEMS) technologies. When the skin that is in contract with the vibration sensor 208 vibrates, vibration sensor 208 may provide an output signal that is proportional to that vibration. Energy converter 210 may convert that output signal into an electrical vibration signal (e.g., an analog or digital signal) that may be provided to processing unit 116 for further processing.

In an embodiment, processing unit 116 may include a processor 204, memory 212, user interface 214, display 216, and communication unit 206. Processor 204 may include a processor as described herein, and memory 212 may include volatile and/or non-volatile memory as described herein. Processor 204 may be in communication with energy converter 210 of the transducer unit 202, as well as the memory 212, user interface 214, display 216, and communication unit 206 of processing unit 116. Processor 204 may receive the vibration signal from energy converter 210, and process that signal to provide a desired physiological signal such as a sonic signal, as described herein.

In some embodiments, it may be desirable for a user to be able to interact with the processing unit 116. Although it will be understood that a user may interact with processing unit 116 in any suitable manner, exemplary interaction includes adjusting settings of the throat microphone 100, observing information relating to the operation of the throat microphone 100, providing software updates to memory 212 of processing unit 116, extracting data from memory 212 of processing unit 116, etc. Accordingly, any suitable user interface 214 and/or display 216 may be provided to facilitate user interaction with processing unit 116. Exemplary user interfaces 214 include buttons, a touch screen, a keyboard, motion-activated interfaces (e.g., based on accelerometer and/or gyroscope), any other suitable user interface, or any combination thereof. Exemplary displays 216 include display screens, LCD interfaces, haptic feedback, any other suitable display that provides information to a user, or any combination thereof. User interface 214 and display 216 may be in communication with processor 204 in any suitable manner (e.g., direct wired connection, a bus of processing unit 116, etc.), which may control the operation of user interface 214 and display 216. It will be understood that although user interface 214 and display 216 are depicted and described as components of processing unit 116, one or both of user interface 214 and display 216 may be located remotely from processing unit 116, for example, at a device 118 in communication with processing unit 116.

Communication unit 206 may be in communication with processor 204 of processing unit 116 and one or more devices 118. Communication unit 206 may communicate with one or more devices 118 in any suitable manner, such as with a modulated data signal via wired (e.g., hard wired, direct acoustic wiring, Ethernet, USB, FireWire, I2C, UART, Thunderbolt, etc.) or wireless (e.g., short range radio, satellite, WiFi, Bluetooth, cellular networks, etc.) connections. In some embodiments, communication unit 206 may receive a desired sonic signal from processor 204 and transmit the desired sonic signal to device 118. It will also be understood that communication unit 206 may facilitate communication of additional communication between processor 204 and device 118. Although it will be understood that communication unit 206 may facilitate communication of any suitable information, in some embodiments the additional information may include control settings, software updates, user interface information, display information, values for secondary physiological phenomena, any other suitable information, or any combination thereof. In addition, it will be understood that communication unit 206 may be in communication with any other suitable devices, components, hardware, or sensors in addition to one or more devices 118, for example, one or more secondary sensors that may provide information that may be used for processing of vibration signals.

Figure 3:
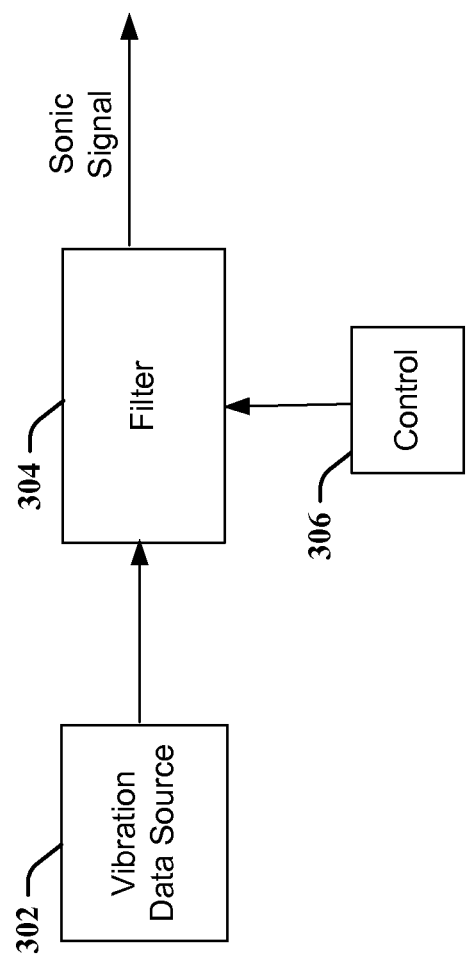
FIG. 3 depicts a non-limiting block diagram of processing of a vibration signal of a throat microphone according to various non-limiting aspects of the subject disclosure.

Turning now to FIG. 3, illustrated is a non-limiting block diagram of processing of a vibration signal of a throat microphone according to various non-limiting aspects of the subject disclosure. Processor 204 may perform the operations depicted in the block diagram of FIG. 3, based on a received vibration signal from converter 210 of transducer 112, data and instructions stored on memory 212, settings and information provided by one or more of user interface 214 or communication unit 206, any other suitable data source, or any combination thereof.

Filter 304 may receive information from vibration data source 302 and control signal source 306. Vibration data source 302 may provide a vibration signal, e.g., directly from converter 210 of transducer 112 or a vibration signal stored in memory 212. Control signal source 306 may provide one or more filter control parameters that are used to control the operation of filter 304, e.g., such that filter 304 outputs a filtered vibration signal that is representative of the desired sonic signal.

In an embodiment, control signal source 306 may determine the filter control parameters without reference to the vibration signal of vibration data source 302. Although any suitable information may be used to determine the filter control parameters, in some embodiments the filter control parameters may be based on preselected settings, external settings, measurements from additional sensors, any other suitable data source, or any combination thereof. As described herein, in some embodiments non-sonic vibrations may be associated with secondary physiological phenomena such as breathing or heartbeat.

A typical resting respiration rate for an adult may range from 12-20 breaths per minute (0.2-0.33 Hz) while a typical resting heart rate for an adult may range from 60-100 beats per minute (1-1.67 Hz). However, respiration rate and heart rate vary significantly based on individual characteristics (e.g., age, sex, and fitness level) and activity levels (e.g., sitting, walking, and exercising). Moreover, the vibration response of a transducer 112 to breathing or heartbeat may also include higher frequency information, e.g., based on harmonics of the base respiration or heart rate. Filter control parameters based on one or more of these physiological phenomena may take into account typical respiration rate and/or heart rates for the general population, typical respiration and/or heart rates for the particular person 102 using the throat microphone 100, actual (e.g., measured) respiration and/or heart rates for the person 102, demographic information of a user, (e.g., age and sex), additional information from other sensors that may be related to respiration and/or heart rates (e.g., activity level), known or calibrated vibration response of a transducer to vibrations caused by respiration and/or heart rates, any other suitable information, or any combination thereof.

Although it will be understood that any suitable filter control parameters may be provided by control signal source 306 based on the secondary physical phenomena, in an exemplary embodiment the filter control parameters may include values related to a cutoff frequency, rolloff, any other suitable filter parameters, or any combination thereof. For example, the fundamental frequency of speech of a typical adult male may range from 85-180 Hz while the fundamental frequency of speech for a typical female may range from 165-255 Hz. In some embodiments, it may be desirable to set a cutoff frequency that excludes vibrations that result from the secondary physiological phenomena, but maintains a significant frequency range around the typical voice frequencies described above. Accordingly, in some embodiments a filter control parameter may be setting that results in a cutoff frequency for a high-pass filter that includes a range to capture speech but excludes much of the energy and information relating to the secondary physiological phenomena.

Although it will be understood that any suitable filter control parameter may be provided to set a cutoff frequency for a high-pass filter (e.g., filter 304), in some embodiments the filter control parameter may be a filter shift value for a digital high pass filter. In an embodiment, once control signal source 306 identifies a cutoff frequency, a filter shift value may n be determined based on a known sampling rate of the vibration signal and the cutoff frequency, according to the following:

$$F_c = -\ln(1-2^{-n})*(fs/2*\pi)$$

where:
Fc=cutoff frequency;
fs=sampling frequency; and
n=shift value

Figure 5:
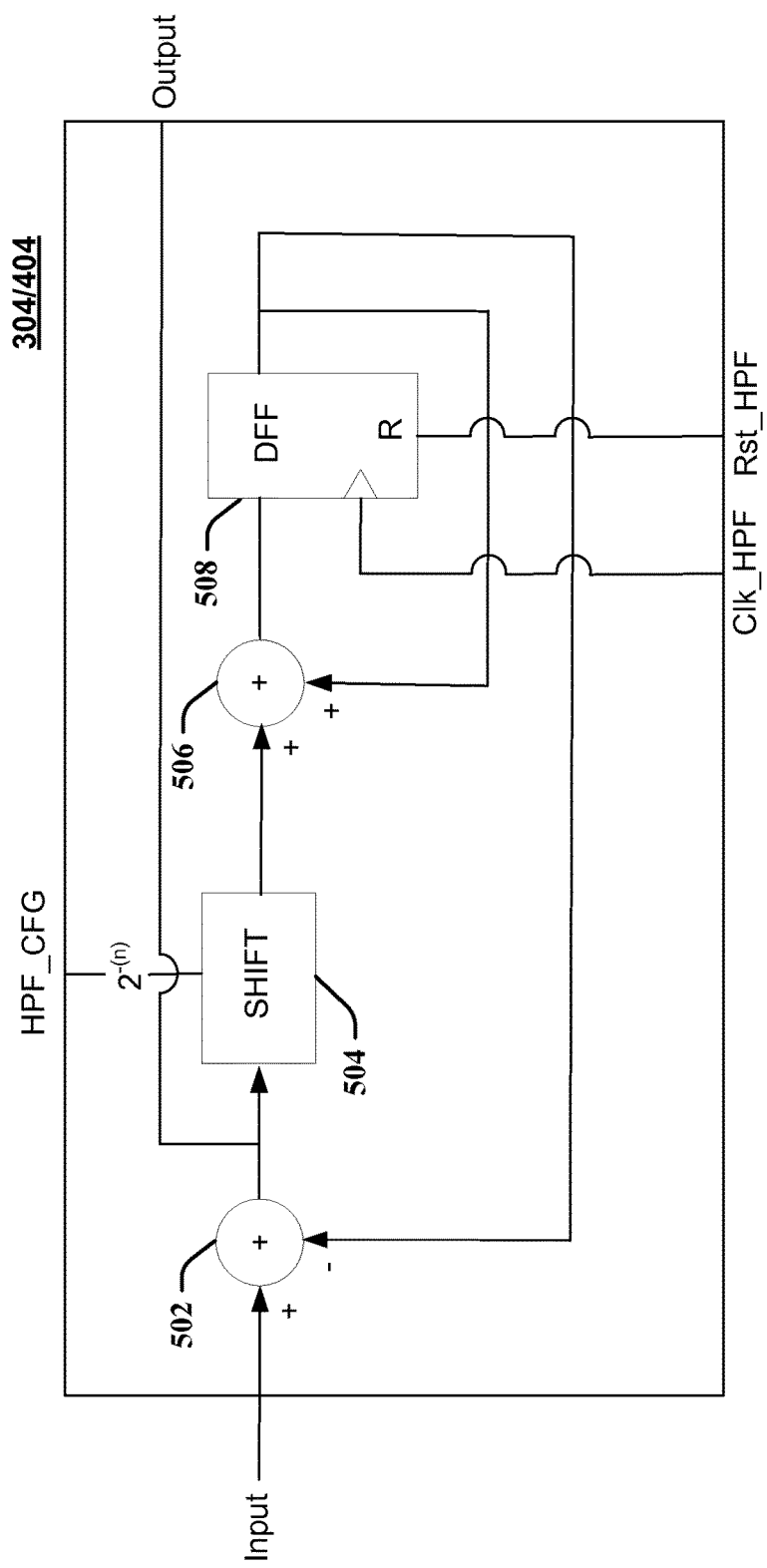
FIG. 5 depicts a non-limiting schematic diagram of an exemplary high-pass filter according to various non-limiting aspects of the subject disclosure.

A shift value calculated according to this relationship may then be provided to a digital high pass filter, for example, the digital high pass filter described in FIG. 5.

In an embodiment, filter 304 may provide an output of a desired sonic signal by filtering the vibration signal from vibration source 302 based on one or more filter control parameters from control signal source 306. Although it will be understood that filter 304 may filter the vibration signal in any suitable manner, in an exemplary embodiment filter 304 may be a high-pass filter that removes energy from the vibration signal that falls below a cutoff frequency determined by the filter control parameter.

Figure 4:
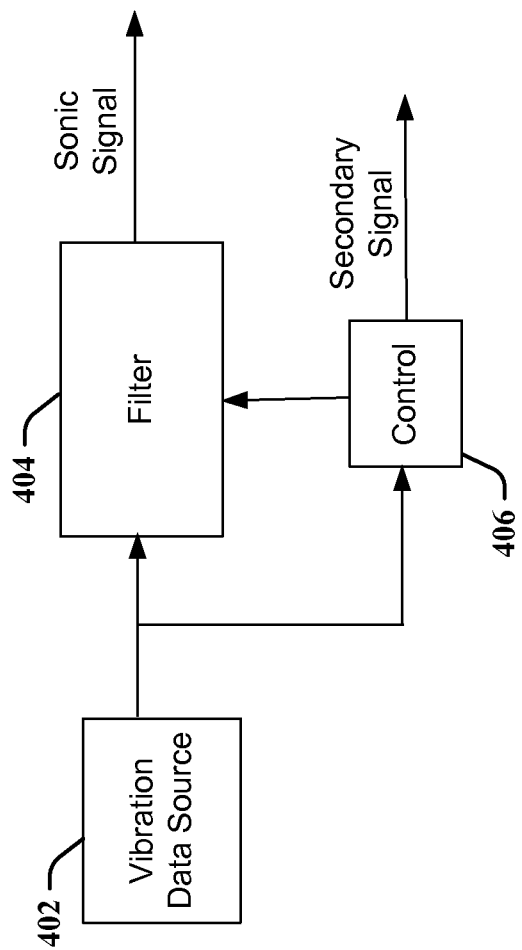
FIG. 4 depicts a non-limiting block diagram of processing of a vibration signal of a throat microphone according to various non-limiting aspects of the subject disclosure.

Turning now to FIG. 4, illustrated is a non-limiting block diagram of processing of a vibration signal of a throat microphone according to various non-limiting aspects of the subject disclosure. Vibration data source 402, filter 404, and control signal source 406 of FIG. 4 are similar to vibration data source 302, filter 304, and control signal source 306 of FIG. 3, except that in the embodiment of FIG. 4 control signal source 406 also receives the vibration signal from vibration data source 402, and in some embodiments, may also provide an output signal related to one or more secondary physiological phenomena.

In an embodiment, control signal source 406 may use the received vibration signal to set filter control parameters based on the actual characteristics of the secondary physiological phenomena that can be determined from the vibration signal. Although any filter control parameters may be determined in any suitable manner, in an embodiment, a shift value associated with a cutoff frequency for a high-pass filter may be determined based on the energy of the vibration signal at frequencies corresponding to the vibrations caused by one or more of the secondary physiological phenomena. Additionally, the actual vibration characteristics of the secondary physiological phenomena may be combined with other information in order to set one or more filter control parameters, such other information including typical respiration rate and/or heart rates for the general population, typical respiration and/or heart rates for the particular person 102 using the throat microphone 100, actual (e.g., measured) respiration and/or heart rates for the person 102, demographic information of a user, (e.g., age and sex), additional information from other sensors that may be related to respiration and/or heart rates (e.g., activity level), known or calibrated vibration response of a transducer to vibrations caused by respiration and/or heart rates, any other suitable information, or any combination thereof.

Turning now to FIG. 5, illustrated is a non-limiting schematic diagram of an exemplary high-pass filter (e.g., filter 304 of FIG. 3 or filter 404 of FIG. 4) according to various non-limiting aspects of the subject disclosure. Although it will be understood that a high-pass filter may be implemented in any suitable manner, in an embodiment, a digital high-pass filter may be implemented as depicted FIG. 5. An exemplary digital high-pass filter may have inputs including the input vibration signal (Input) a high pass filter configuration signal (HPF_CFG), a clock signal (Clk_HPF), and a reset signal (Rst_HPF). Outputs may include the desired sonic signal (Output). The digital high pass filter may include subtractor 502, shift register 504, adder 506, and digital flip-flop 508.

Subtractor 502 may receive on its positive side a stream of digital samples associated with the input vibration signal and on its negative side stream of digital samples associated with energy at the frequencies to be removed by the high pass filter. The resulting output signal of subtractor 502 may be provided as the output desired sonic signal and also to the digital processing circuitry of the high pass filter (e.g., shift register 504, adder 506, and digital flip flop 508), which in turn determines the signal to be removed based on the output of subtractor 502 and a shift value n (e.g., the filter control parameter determined by control signal source 306/406), as is known in the art.

Figure 6:
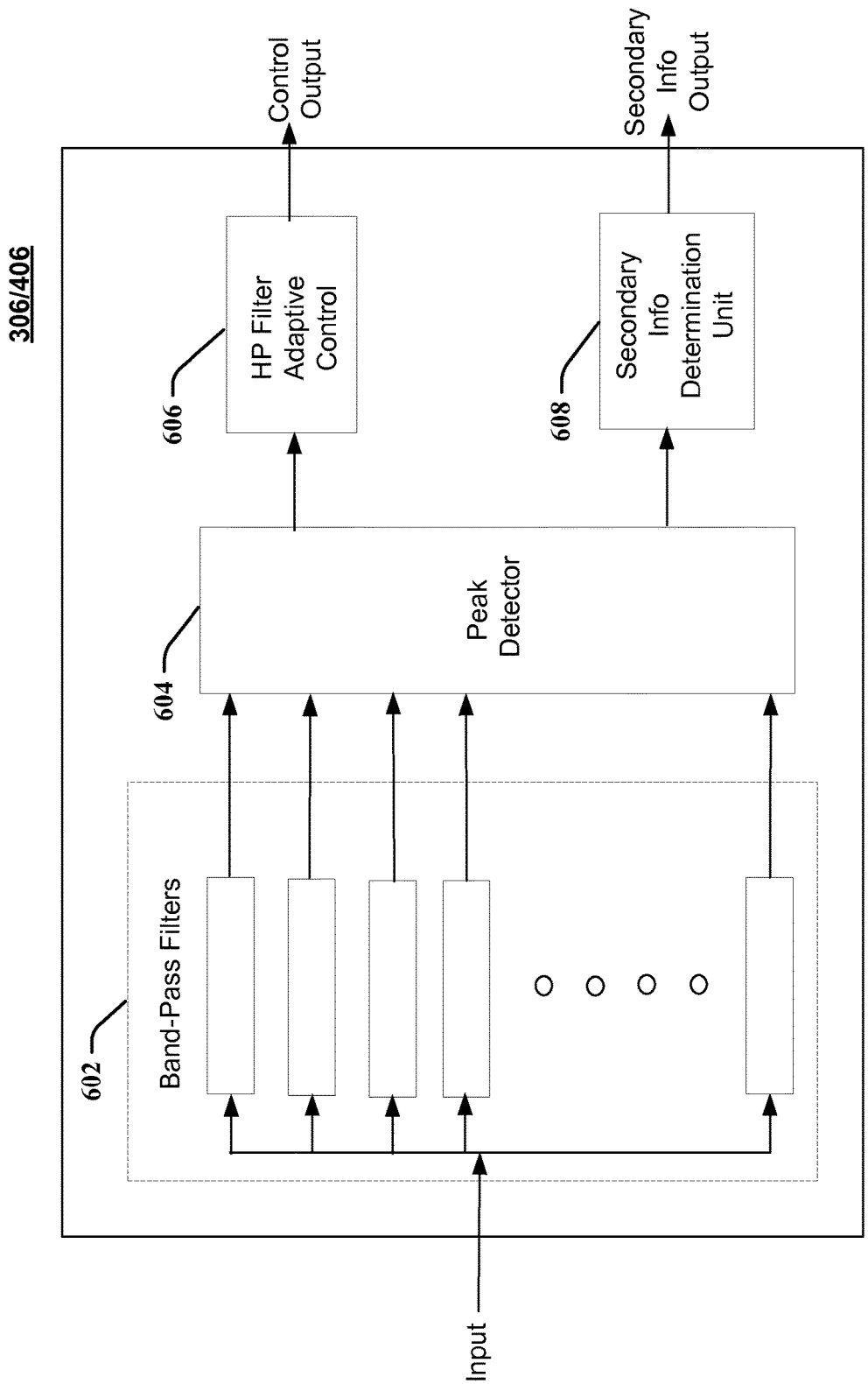
FIG. 6 depicts a non-limiting schematic diagram of an exemplary control signal source according to various non-limiting aspects of the subject disclosure.

Turning now to FIG. 6, illustrated is a non-limiting schematic diagram of an exemplary control signal source according to various non-limiting aspects of the subject disclosure. Although a control signal source (e.g., control signal source 306/406) may be implemented in any suitable manner, in an embodiment control signal source may include filter bank 602, peak detector 604, high-pass filter adaptive control 606, and secondary physiological phenomena determination unit 608.

Filter bank 602 may include a plurality of band-pass filters, each including a pass band associated with a subset of the frequencies associated with vibrations caused by the secondary physiological phenomena. Although the frequency bands of each band-pass filter may be determined in any suitable manner, in an exemplary embodiment the band-pass filters may cover adjacent frequency ranges commonly associated with the vibratory response of the transducer 112 to the secondary physiological phenomena. In some embodiments, the pass bands for the filters may be configurable, for example, based on user-defined settings, measurements from secondary sensors, any other suitable information, or any combination thereof.

The vibration signal (e.g., from vibration signal source 302/402) may be provided as an input to each of the band-pass filters of the filter bank 602. Each band-pass filter may provide an output signal that includes the portion of the vibration signal corresponding to the respective pass band of the band-pass filter. In this manner, each of the output signals from filter bank 602 will have a signal energy that corresponds to the energy of the vibration signal within the frequency range associated with the respective pass band of the band-pass filter. All of the output signals from filter bank 602 are then provided to peak detector 604.

In an embodiment, peak detector 604 may determine the energy of each of the output signals from filter bank 602 in order to identify one or more frequency bands associated with the vibrations caused by the secondary physiological phenomena. Based on the determined energies, peak detector 604 may provide outputs to high-pass filter adaptive control 606 and secondary physiological phenomena determination unit 608. Although it will be understood that any suitable data output may be provided to high-pass filter adaptive control 606 and secondary physiological phenomena determination unit 608 in any suitable manner, in an exemplary embodiment an array of data associating each pass band with an energy level may be provided to each of high-pass filter adaptive control 606 and secondary physiological phenomena determination unit 608.

High-pass filter adaptive control 606 may process the data array to determine a characteristic of the vibration signal and output a filter control parameter based on that characteristic. Although any suitable characteristic of the vibration signal may be determined, in an embodiment, the characteristic may include one or more parameters for a high-pass filter (e.g., filter 304 or filter 404) such as a cutoff frequency, rolloff, etc. The characteristic may be determined based on the energies for each of the pass bands. In an embodiment, a characteristic such as cutoff frequency may be set based on the highest pass band having an energy level that exceeds an energy threshold, which may be associated with a signal energy that is likely to result in interference with the desired sonic signal. The cutoff frequency may be associated with this pass band (e.g., at the highest frequency of the pass band) and may be used to determine one or more filter control parameters (e.g., a filter shift value) as described herein. The filter control parameter may then be provided to a filter such as filter 304 or filter 404.

Secondary physiological phenomena determination unit 608 may process the data array to determine a value for one or more secondary physiological phenomena. Although any suitable secondary physiological phenomena may be determined based on the data array, in an embodiment, the data array may be used to determine values for respiration rate and/or heart rate. The values for the secondary physiological phenomena may be determined based on the energies associated with the pass bands that are known to include information relating to the secondary physiological phenomena. For example, as described herein, it may be known that a particular frequency range may be associated with respiration and/or heartbeat, and that a frequency range associated with heartbeat will typically be significantly greater than a frequency range associated with respiration. In an embodiment, a plurality of candidate maximum energy values may be determined within the frequency range associated with the secondary physiological phenomena, and values for the secondary physiological phenomena may be determined based on these values and known relationships between the secondary physiological phenomena. For example, a value for each of respiration rate and heart rate may be determined based on the center frequency of the pass band for the respective band-pass filter associated with each of respiration rate and heart rate. The values for the secondary physiological phenomena may then be output, for example, to communication unit 206, memory 212, and/or display 216.

While several example embodiments are provided, it is noted that aspects of this disclosure are not limited to the exemplary embodiments. As such, the various embodiments disclosed herein can be applied to numerous applications. In exemplary embodiments, systems and methods described herein can be applied to tactical communication systems, smart phones, hand held gaming devices, hand held electronics, notebook computers, desktop computers, and the like. Such systems can utilize aspects disclosed herein to determine characteristics associated with acoustic signals, such as for speech recognition, pressure detection, or the like.

Figure 7:
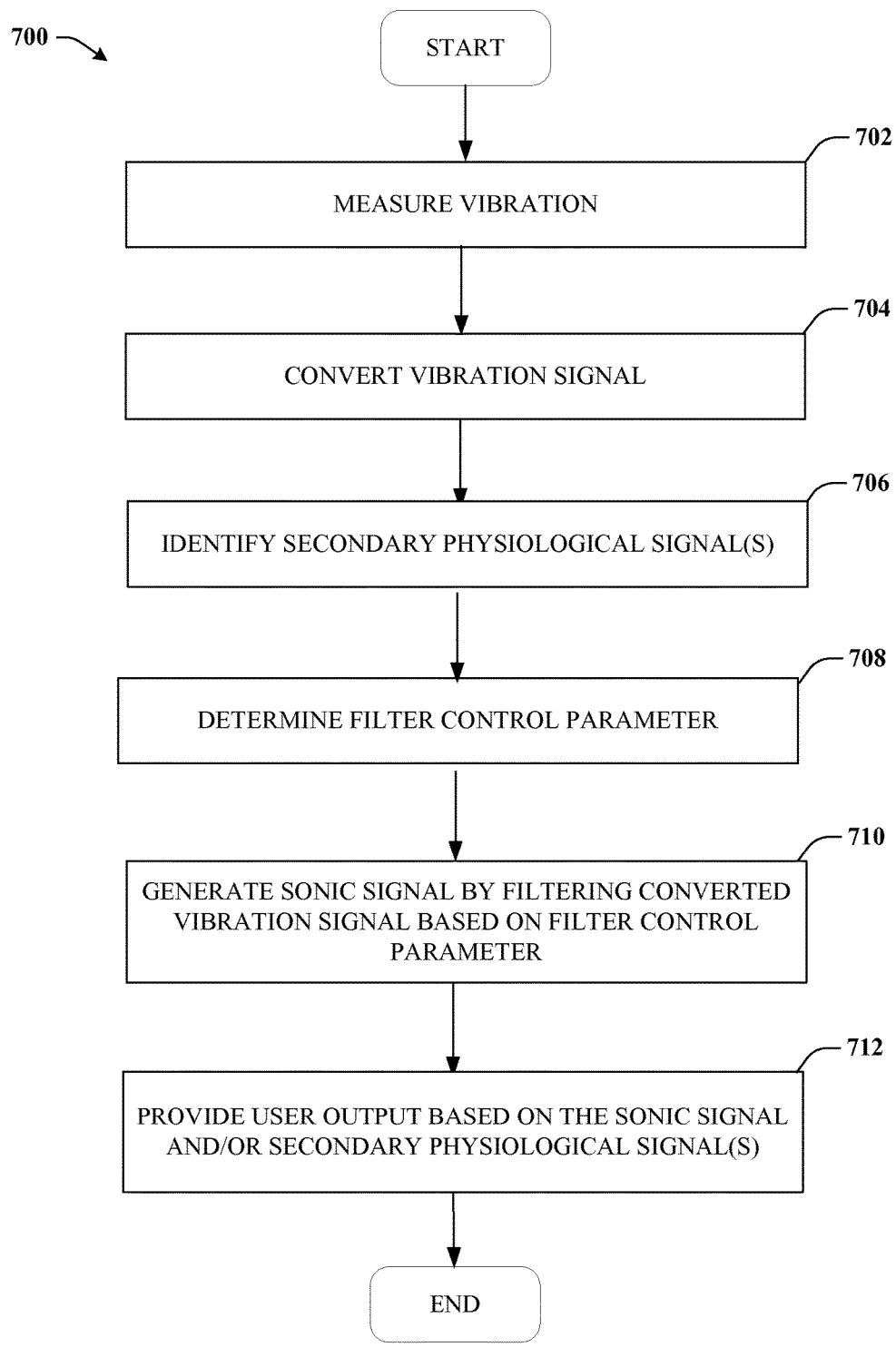
FIG. 7 depicts an example flowchart of steps for providing a sonic signal from a vibration signal in accordance with certain embodiments of this disclosure.

In view of the subject matter described supra, methods that can be implemented in accordance with the subject disclosure will be better appreciated with reference to the flowchart of FIG. 7. While for purposes of simplicity of explanation, the methods are shown and described as a series of blocks, it is to be understood and appreciated that such illustrations or corresponding descriptions are not limited by the order of the blocks, as some blocks may occur in different orders and/or concurrently with other blocks from what is depicted and described herein. Any non-sequential, or branched, flow illustrated via a flowchart should be understood to indicate that various other branches, flow paths, and orders of the blocks, can be implemented which achieve the same or a similar result. Moreover, not all illustrated blocks may be required to implement the methods described hereinafter.

Exemplary Methods

FIG. 7 depicts an example flowchart of steps for providing a sonic signal from a vibration signal in accordance with certain embodiments of this disclosure. As a non-limiting example, exemplary method 700 can facilitate providing a sonic signal with a throat microphone as described herein (e.g., throat microphone 100).

Method 700 can begin at 702, where the method includes measuring vibration. In an embodiment and as described herein, one or more transducers 112 may be in contact with the skin of a person 102 in the region of the larynx, in a manner that permits a vibration sensor 208 to sense vibrations 110 of the skin.

The method can continue at 704, where the method includes converting the measured vibration into a vibration signal. In an embodiment and as described herein, the vibration sensed by vibration sensor 208 of transducer 112 is converted into an electrical vibration sensor by energy converter 210. The vibration signal that is output from energy converter 210 may be provided to a processor 204 of processing unit 116.

The method can continue at 706, where the method includes identifying one or more secondary physiological phenomena signals based on the vibration signal. In an embodiment and as described herein, a control signal source (e.g., control signal source 306/406 of processor 204) may determine a frequency and/or frequency range associated with one or more of the one or more secondary physiological phenomena, for example, based on a data array provided by a filter bank 602 and peak detector 604. The data array may be provided to one or more of high-pass filter adaptive control 606 and/or secondary physiological phenomena determination unit 608.

The method can continue at 708, where the method includes generating one or more filter control parameters. In an embodiment and as described herein, a control signal source (e.g., control signal source 306/406 of processor 204) may determine the filter control parameter based on a characteristic (e.g., cutoff frequency) determined based on the information (e.g., a data array) provided to a high-pass filter adaptive control 606 by peak detector 604. In an embodiment, the filter control parameter may be a shift value associated with a digital high-pass filter, and may be output to a filter 304/306 of processor 204.

The method can continue at 710, where the desired sonic signal may be generated by filtering the vibration signal based on the one or more filter control parameters. In an embodiment and as described herein, a filter 304/404 of processor 204 (e.g., the digital high-pass filter of FIG. 5) may receive both the vibration signal and shift value, and remove lower frequency content of the vibration signal that is associated with the secondary physiological phenomena, based on the shift value. The output signal of the filter 304 may be a desired sonic signal and may be provided to one or more of communication unit 206, memory 212, and/or display 216.

The method can continue at 712, where an output may be provided based on the desired sonic signal and/or the secondary physiological signal. In an embodiment and as described herein, processor 204 may output a desired sonic signal and/or determined values associated with the secondary physiological phenomena. These may be provided to communication unit 206, which in turn may transmit the outputs to a suitable device 118, as described herein.

What has been described above includes examples of the embodiments of the present disclosure. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize. Moreover, use of the term "an embodiment" or "one embodiment" throughout is not intended to mean the same embodiment unless specifically described as such.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this application, the terms "component," "module," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer readable medium; or a combination thereof.

Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Computing devices typically include a variety of media, which can include computer-readable storage media and/or communications media, in which these two terms are used herein differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

What is claimed is:

1. A system for providing a desired physiological signal based on vibrations of a throat area of a person, comprising:
    a vibration sensor;
    a processor coupled to the vibration sensor, wherein the processor is configured to receive a vibration signal from the vibration sensor, identify a characteristic of the vibration signal that is associated with a secondary physiological phenomena, determine a filter control parameter based on the characteristic, and provide the desired physiological signal based on the filter control parameter and the vibration signal; and
    a communication unit coupled to the processor and in communication with a device, wherein the communication unit transmits the desired physiological signal to the device.

2. The system of claim 1, wherein the characteristic is a cutoff frequency and the vibration signal is filtered with a high-pass filter based on the filter control parameter.

3. The system of claim 2, wherein the processor is configured to calculate a filter shift value based on the cutoff frequency and a sampling rate of the filter, and provide the filter shift value as the filter control parameter.

4. The system of claim 1, wherein the secondary physiological phenomena comprises at least one of respiration or heartbeat.

5. The system of claim 1, wherein the desired physiological signal comprises a sonic signal.

6. The system of claim 1, wherein the processor is configured to provide the vibration signal to a plurality of band-pass filters, determine an energy associated with an output of each of the plurality of band-pass filters, and identify the characteristic based on one or more of the determined energies.

7. The system of claim 6, wherein the processor is configured to provide a signal representative of the secondary physiological phenomena based on the one or more determined energies.

8. The system of claim 1, wherein the communication unit is a wireless transmitter.

9. The system of claim 8, wherein processor is configured to encode the desired physiological signal for transmission by the wireless transmitter.

* * * * *